(12) United States Patent
Jacobsen et al.

(10) Patent No.: US 9,975,850 B2
(45) Date of Patent: May 22, 2018

(54) PROCESS FOR THE MANUFACTURE OF IDALOPIRDINE VIA HYDROGENATION OF AN IMINE

(71) Applicant: H. Lundbeck A/S, Valby (DK)

(72) Inventors: Mikkel Fog Jacobsen, Frederiksberg (DK); Florian Anton Martin Huber, Dolo (IT)

(73) Assignee: H. LUNDBECK A/S, Valby (DK)

( * ) Notice: Subject to any disclaimer, the term of this patent is extended or adjusted under 35 U.S.C. 154(b) by 0 days. days.

(21) Appl. No.: 15/480,647

(22) Filed: Apr. 6, 2017

(65) Prior Publication Data

US 2017/0291874 A1    Oct. 12, 2017

(30) Foreign Application Priority Data

Apr. 8, 2016 (DK) .................................. 2016 00211

(51) Int. Cl.
*C07D 209/14* (2006.01)
*B01D 3/36* (2006.01)

(52) U.S. Cl.
CPC .............. *C07D 209/14* (2013.01); *B01D 3/36* (2013.01)

(58) Field of Classification Search
CPC .................................................... C07D 209/14
See application file for complete search history.

(56) References Cited

U.S. PATENT DOCUMENTS

| 7,157,488 | B2 | 1/2007 | Chen et al. | |
|---|---|---|---|---|
| 2011/0152539 | A1* | 6/2011 | Therkelsen | C07D 209/16 |
| | | | | 548/503 |

FOREIGN PATENT DOCUMENTS

| EP | 1859798 A1 | 11/2007 |
|---|---|---|
| WO | WO 2011/076212 | 6/2011 |
| WO | WO 2016/091997 | 6/2016 |

OTHER PUBLICATIONS

Berge, S.M., et al. (1977) "Pharmaceutical Salts," J. Pharma. Sci. 66:1-19.
Abd Razik, B.M., et al., "Ionic liquid mediated synthesis and molecular docking study of novel aromatic embedded Schiff bases as potent cholinesterase inhibitors," Bioorganic Chemistry, vol. 57, pp. 162-168 (Nov. 4, 2014).
International Search Report and Written Opinion dated May 24, 2017 in PCT/EP2017/058178 (11 total pages).

* cited by examiner

*Primary Examiner* — Shawquia Jackson
(74) *Attorney, Agent, or Firm* — Wilmer Cutler Pickering Hale and Dorr LLP

(57) ABSTRACT

The present invention relates to the preparation of N-(2-(6-fluoro-1H-indol-3-yl)-ethyl)-3-(2,2,3,3-tetrafluoro-propoxy)-benzylamine (Compound I), INN-name idalopirdine, and pharmaceutically acceptable salts thereof:

Compound (I)

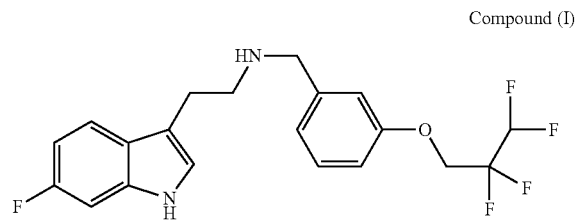

18 Claims, No Drawings

PROCESS FOR THE MANUFACTURE OF IDALOPIRDINE VIA HYDROGENATION OF AN IMINE

CROSS-REFERENCE TO RELATED APPLICATIONS

This application claims priority to Danish Patent Application No. PA201600211, filed Apr. 8, 2016, which application is herein incorporated by reference in its entirety.

FIELD OF THE INVENTION

The present invention relates to the preparation of N-(2-(6-fluoro-1H-indol-3-yl)-ethyl)-3-(2,2,3,3-tetrafluoropropoxy)-benzylamine, INN-name idalopirdine, and pharmaceutically acceptable salts thereof.

BACKGROUND ART

N-(2-(6-fluoro-1H-indol-3-yl)-ethyl)-3-(2,2,3,3-tetrafluoropropoxy)-benzylamine is a potent and selective 5-HT$_6$ receptor antagonist which is currently in clinical development. Its chemical structure is depicted below as Compound (I):

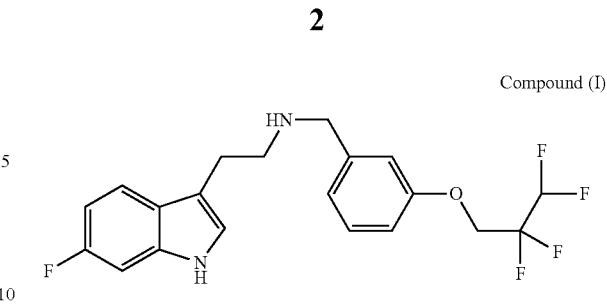

The synthesis of N-(2-(6-fluoro-1H-indol-3-yl)-ethyl-(2,2,3,3-tetrafluoropropoxy)-benzylamine, its use for the treatment of disorders such as cognitive dysfunction disorders, and pharmaceutical compositions comprising this substance are disclosed in U.S. Pat. No. 7,157,488 which further describes the preparation of the corresponding mono-hydrochloride salt.

An improved method for the manufacture of Compound (I) or salt thereof is disclosed in international patent application WO2011/076212.

Further, WO2016/091997 discloses the synthesis of N-(2-(6-fluoro-1H-indol-3-yl)-ethyl)-3-(2,2,3,3-tetrafluoropropoxy)-benzylamine by use of a supported Ni-catalyst with the use of sodiumborohydride as a reducing agent.

The final steps in the preparation of Compound (I) or pharmaceutically acceptable salts thereof as disclosed in WO2011/076212 are outlined in Scheme A:

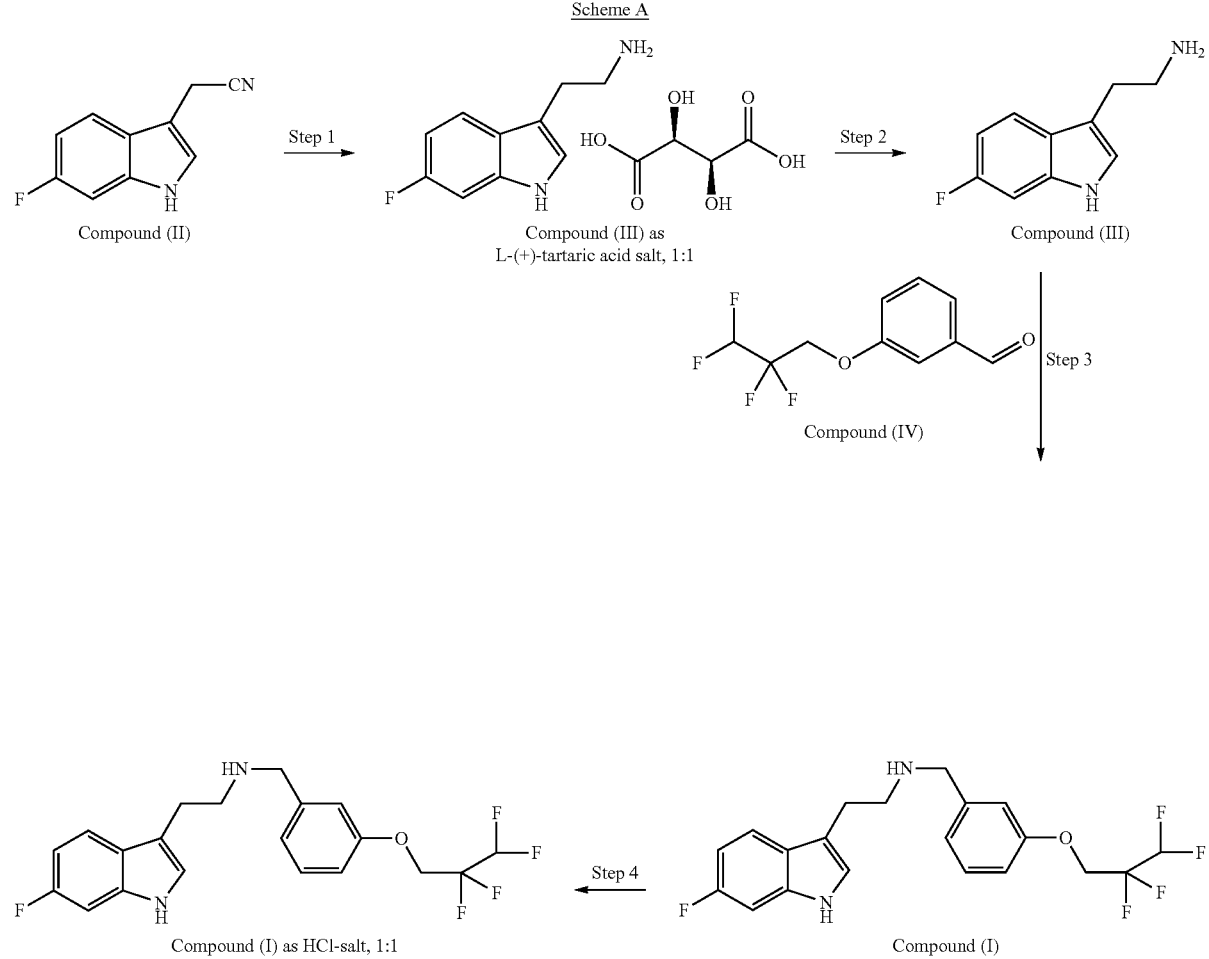

The synthesis of Compound (IV) can conveniently be carried out as outlined below:

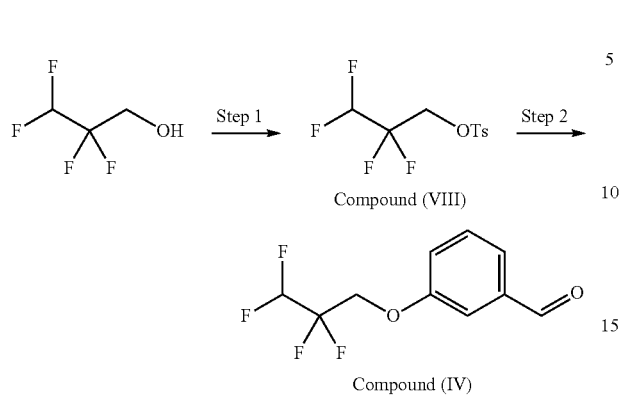

The synthesis of Compound (IV) comprises the following steps:
1) Subjecting 2,2,3,3-tetrafluoro-1-propanol to tosylation to yield Compound (VIII);
2) and reacting Compound (VIII) in a displacement reaction with 3-hydroxybenzaldehyde in the presence of a base to yield Compound (IV).

The steps in the synthesis of Compound (I) as described above in scheme A consist of:
1) Hydrogenation of Compound (II) in the presence of a catalyst to obtain Compound (III), and isolation as L-(+)-tartaric acid salt (1:1) thereof (Step 1, Scheme A)
2) liberating Compound (III) from the L-(+)-tartaric acid salt (1:1) thereof (Step 2, Scheme A) to form the free base of Compound (III)
3) reacting the free base of Compound (III) with Compound (IV) in the presence of a reductant, specifically sodium borohydride to form Compound (I) (Step 3, Scheme A)
4) forming the HCl-salt (1:1) of Compound (I) (Step 4, Scheme A).

However, the reduction with sodium borohydride in step 3 suffers from a number of drawbacks:
a) Long quenching times
b) Large amounts of waste are generated
c) Many unit operations (e.g. layer washings)
d) The formation of alcohol Compound (IX) also occurs in step 3 due to reduction of Compound (IV) with sodium borohydride, which leads to lowering of the yield of Compound (I):

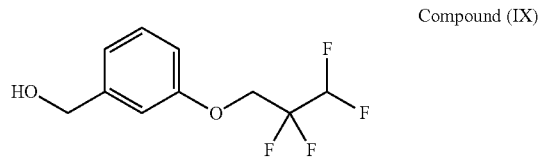 [SMILES: OCc1cccc(OCC(F)(F)C(F)F)c1]

e) The formation of stable boron-amine complexes, such as Compound (X), which are not easily converted into Compound (I) or removed:

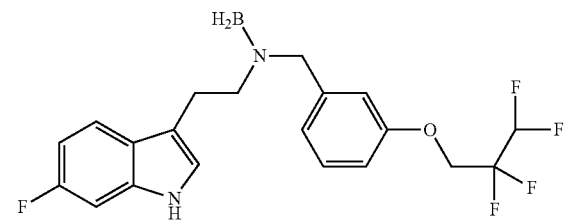

f) The formation of enol ether Compound (XI) (E- and/or Z-isomer) which resides as an impurity in Compound (I) and salts thereof:

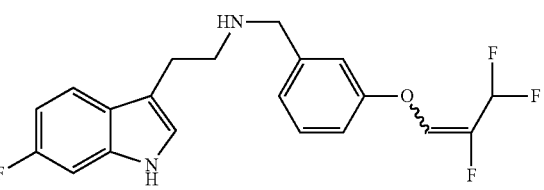

Therefore, a more clean and productive process for the formation of Compound (I) is desirable. Such a process has been developed, and is disclosed in this patent application.

SUMMARY OF THE INVENTION

The present invention discloses a further development of the above discussed process where, in this new process, Compound (III) and Compound (IV) are reacted to form the imine Compound (V) which subsequently is reduced to form Compound (I) by hydrogenation, thus avoiding the use of sodium borohydride.

In one embodiment of the invention is disclosed a process for the preparation of Compound (V)

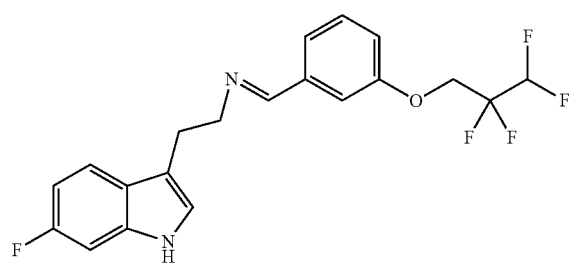

comprising the following steps:
1) Mixing Compound (III) and Compound (IV) in a solvent or solvent mixture, with or without azeotropical separation of water
2) Isolating the precipitated Compound (V).

In another aspect of the invention is disclosed a process for the preparation of Compound (I) or a pharmaceutically acceptable salt thereof comprising the steps of:
1) Forming Compound (V) from Compound (III) and Compound (IV) in a solvent or solvent mixture with or without removal of water and precipitating and isolating Compound (V) as a solid:

Compound (V)

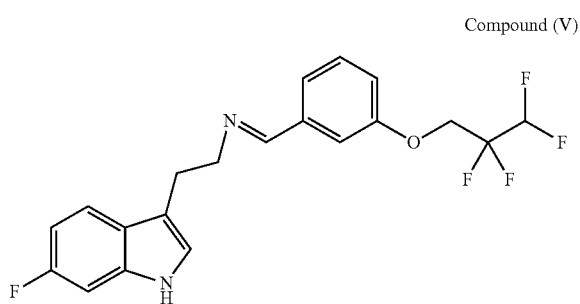 [SMILES: Fc1ccc2c(CC/N=C/c3cccc(OCC(F)(F)C(F)F)c3)c[nH]c2c1]

2) Reacting Compound (V) with hydrogen in the presence of a transition metal catalyst in a solvent or solvent mixture to form Compound (I)

3) Isolating Compound (I), optionally as a salt.

Isolated compound (V) can be obtained with a high purity (>99% UV area HPLC), even when starting from Compound (III) with a low purity (around 92% UV area HPLC).

In another aspect of the invention is disclosed a process for the preparation of Compound (I) or a pharmaceutically acceptable salt thereof comprising the steps of:

1) Forming Compound (V) from Compound (III) and Compound (IV) in a solvent or solvent mixture
2) Reacting the mixture with hydrogen in the presence of a transition metal catalyst in a solvent or solvent mixture to form Compound (I)
3) Isolating Compound (I), optionally as a salt.

DETAILED DESCRIPTION OF THE INVENTION

The process of the present invention takes advantage of the use of hydrogen as reductant instead of sodium borohydride. The disclosed process has the advantages discussed above and generates less waste, is cheaper, and allows for an easier isolation of Compound (I) or pharmaceutically acceptable salts thereof, compared to the use of the reductant sodium borohydride as described in WO2011/076212.

Also, fewer steps (and hence, unit operations in the plant) are needed in the process of the present invention compared to process for obtaining Compound (I) as described in WO2011/076212, since there is no need to isolate the L-(+)-tartaric acid salt (1:1) of Compound (III), and workup of Compound (I) is easier.

Another advantage is that in the formation of Compound (I) via hydrogenation of Compound (V), as disclosed herein, byproducts Compound (IX), Compound (X) and Compound (XI) are not observed.

Hydrogenation of Compound (V) provides Compound (I) with a good purity, such as more than 95% or even more than 99%, measured as UV area HPLC. Surprisingly, hydrogenation of Compound (V) with certain transition metal catalysts (e.g. Pd/C) disclosed herein yields Compound (I) with either non-detectable or very low amounts of byproduct Compound (VI) resulting from a N-debenzylation reaction of Compound (I):

Compound (VI)

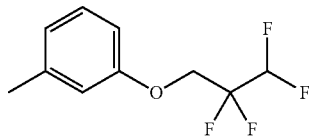

Upon salt formation the purity of compound (I) can be further improved, If necessary the salt can be recrystallized and the purity is improved further (>99.7% UV area HPLC).

Thus, in an embodiment (E1) the present invention relates to a process for the preparation of N-(2-(6-fluoro-1H-indol-3-yl)-ethyl)-3-(2,2,3,3-tetrafluoropropoxy)-benzylamine (Compound (I)), and pharmaceutically acceptable salts thereof, comprising the steps of:

1) forming Compound (V) from Compound (III) and Compound (IV) in a solvent or solvent mixture with or without removal of water, and
2) reacting Compound (V) with hydrogen in the presence of a transition metal catalyst in a solvent or a solvent mixture with or without the presence of an acid to form Compound (I), and
3) optionally adding an acid to precipitate Compound (I) as a salt.

In another embodiment (E2) of the present invention is disclosed a process for the preparation of Compound (I) and pharmaceutically acceptable salts thereof comprising the following steps:

1) forming Compound (V) from Compound (III) and Compound (IV) in a solvent or solvent mixture with or without removal of water, and
2) cooling the mixture to precipitate Compound (V) as a solid, and isolating Compound (V)
3) reacting Compound (V) with hydrogen in the presence of a transition metal catalyst in a solvent or a solvent mixture, with or without the presence of an acid to form Compound (I), and
4) optionally adding an acid to precipitate Compound (I) as a salt.

In a first particular embodiment of any of embodiment (E1) and (E2) Compound (V) is formed in an alcoholic solvent in step 1 of the any of the embodiments.

In a more particular embodiment of the previous embodiment the alcoholic solvent is IPA.

In a second particular embodiment of any of embodiment (E1) and (E2) Compound (V) is formed in a hydrocarbon solvent in step 1 of the any of the embodiments.

In a more particular embodiment of the previous embodiment the solvent is toluene or heptane or a solvent mixture of toluene and heptane.

In a more particular embodiment of the previous embodiment the heptane is n-heptane.

In a third embodiment (E3) the temperature of the reaction mixture in which Compound (V) (step 1) is formed is between 0° C. and 100° C., preferably between 40° C. and 100° C.

In a more particular embodiment of the previous embodiment the temperature of the reaction mixture is between 60° C. and 80° C., such as between 70° C. and 80° C., in particular about 75° C.

In a fourth embodiment (E4) precipitation of Compound (V) (step 2 of (E2)) is done by cooling the mixture to between −10° C. and 30° C.

In a more particular embodiment of the previous embodiment the mixture is cooled to room temperature, such as 15° C. to 30° C. in order to precipitate Compound (V).

In a fifth embodiment (E5) Compound (V) is obtained with a purity above 99% (measured as UV area HPLC) starting from Compound (III) and Compound (IV) having a purity in the range of 90%-99% (measured as UV area HPLC), such as 90%-95% (measured as UV area HPLC).

In an embodiment (E6) of any of embodiments (E1) and (E2) the hydrogenation is carried out in a solvent comprising an ether, ester, alcohol, or hydrocarbon or a solvent mixture of any of the aforementioned solvents.

In a particular embodiment of the previous embodiment the hydrogenation is carried out in solvent or solvent mixture which is chosen from the group consisting of THF, EtOAc, IPA and toluene, or mixtures thereof.

In an embodiment (E7) of any of embodiments (E1) and (E2) water is removed in step 1 by azeotropic distillation.

In an embodiment (E8) of any of embodiments (E1) and (E2) the hydrogenation of Compound (V) is carried out at a hydrogen pressure of 1 bar to 10 bar, such as 1 bar to 8 bar, such as 2 bar to 6 bar. In a particular embodiment the pressure is 1 bar.

In an embodiment (E9) of embodiment (E1) and (E2) the hydrogenation of Compound (V) is carried out in the temperature range 0° C. to 100° C., such as between 20° C. and 80° C., such as between 20° C. and 60° C., such as between 20° C. and 40° C., such as between 20° C. and 30° C.

In a particular embodiment of the previous embodiment the hydrogenation is carried out at room temperature, such as in the range of 15° C. to 30° C.

In a particular (E10) embodiment of the embodiments (E1) and (E2) the transition metal catalyst comprises a metal selected from the group consisting of iridium, rhodium, platinum, ruthenium, copper and palladium.

In a more particular embodiment of the previous embodiment the hydrogenation is carried out in the presence of a transition metal catalyst supported on any of silicium oxide, alumina, carbon or mixtures thereof.

In a particular embodiment (E11) of the previous embodiment the hydrogenation is carried out in the presence of palladium supported on carbon (Pd/C).

In a more particular embodiment of the previous embodiment the hydrogenation is carried out in the presence of palladium supported on carbon (Pd/C) with a loading (in mol %) between 0.05 and 0.1.

In an embodiment the hydrogenation is carried out in the presence of an acid additive.

In a particular embodiment of the previous embodiment the hydrogenation is carried out in the presence of an acid chosen from the group consisting of AcOH, MsOH, TFA, HCl, and sulfuric acid.

In a more particular embodiment of the previous embodiment the hydrogenation is carried out in the presence of an acid chosen from AcOH or MsOH.

In an embodiment (E12) of embodiments (E1) and (E2) Compound (I) is precipitated as a salt by addition of an acid to obtain the corresponding acid addition salt.

In a particular embodiment of the previous embodiment Compound (I) is precipitated as a pharmaceutically acceptable acid addition salt.

In a particular embodiment of the previous embodiment Compound (I) is precipitated as the 1:1 HCl salt.

Compound (I) forms pharmaceutically acceptable acid addition salts with a wide variety of organic and inorganic acids and include the physiologically acceptable salts which are often used in pharmaceutical chemistry. Such salts are also part of this invention. Such salts include the pharmaceutically acceptable salts listed in Berge, S. M. et al., *J. Pharm. Sci.*, 1977, 66, 1-19, which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptarioate, hippurate, lactate, malate, maleate, hydroxymaleate, malonate, mandelate, mesylate, nicotinate, isonicotinate, oxalate, phthalate, teraphthalate, propiolate, propionate, phenylpropionate, salicylate, sebacate, succinate, suberate, benzenesulfonate, p-bromobenzenesulfonate, chlorobenzene-sulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

The following abbreviations are used throughout the description:

"ND" is not detected.
"IPA" is 2-propanol
"THF" is tetrahydrofuran
"EtOAc" is ethyl acetate
"AcOH" is acetic acid
"MsOH" is methanesulfonic acid
"TFA" is trifluoroacetic acid
"DEA" is diethylamine
"aq" is aqueous.
"rt" is room temperature.
"approx." is approximately
"min" is minutes
"h" is hours
"g" is grams.
"mL" is milliliter.
"w/w" is weight per weight.
"v/v" is volume per volume.
"LC-MS" is liquid chromatography-mass spectrometry
"HPLC" is high performance liquid chromatography
"Pd/C" is palladium on charcoal.
"Pt/C" is platinum on charcoal.
"Rh/Alumina" is rhodium on aluminium oxide.
"Ru/C" is ruthenium on carbon
"Ir/CaCO$_3$" is iridium on calcium carbonate
"Cu/C" is copper nanoparticles in charcoal
"PRICAT™" is the trademark for a series of supported catalysts with/without added promotors, from Johnson Matthey Ltd.
"Arbocell BC200™" is the trademark for fibrous cellulose from J. Rettenmaier & Söhne GmbH.

EXPERIMENTAL SECTION

General Experimental

Unless otherwise stated, all reactions were carried out under nitrogen. Reactions were monitored by LC-MS. All reagents were purchased and used without further purification. NMR spectra were recorded at 500 or 600 MHz ($^1$H NMR), and calibrated to the residual solvent peak. The following abbreviations are used for NMR data: s, singlet; bs, broad singlet; d, doublet; t, triplet; m, multiplet. Coupling constants are rounded to nearest 0.5 Hz.

LC-MS Method:

Acquity UPLC BEH C18 1.7 μm column; 2.1×50 mm operating at 60° C. with flow 1.2 mL/min of a binary gradient consisting of water+0.1% formic acid (A) and acetonitrile+5% water+0.1% formic acid (B). UV detection at 254 nm.

HPLC Method:

Zorbax Bonus-RP 5 μm column, 2.6×250 mm operating at 30° C. with flow 1.0 mL/min of a binary gradient consisting of water and acetonitrile, with 0.5% DEA added, buffered to pH 2.3 with TFA. UV detection at 280 nm.

Compound List:
- (I): 2-(6-fluoro-1H-indol-3-yl)-N-(3-(2,2,3,3-tetrafluoropropoxy)benzyl)ethan-1-amine
- (II): 2-(6-fluoro-1H-indol-3-yl)acetonitrile
- (III): 2-(6-fluoro-1H-indol-3-yl)ethan-1-amine
- (IV): 3-(2,2,3,3-tetrafluoropropoxy)benzaldehyde
- (V): (E)-N-(2-(6-fluoro-1H-indol-3-yl)ethyl)-1-(3-(2,2,3,3-tetrafluoropropoxy)phenyl)methanimine
- (VI): 1-methyl-3-(2,2,3,3-tetrafluoropropoxy)benzene
- (VII): 2-(6-fluoro-1H-indol-3-yl)-N,N-bis(3-(2,2,3,3-tetrafluoropropoxy)benzyl)ethan-1-amine
- (VIII): 2,2,3,3-tetrafluoropropyl 4-methylbenzenesulfonate
- (IX): (3-(2,2,3,3-tetrafluoropropoxy)phenyl)methanol
- (X): N-(2-(6-fluoro-1H-indol-3-yl)ethyl)-N-(3-(2,2,3,3-tetrafluoropropoxy)benzyl)boranamine
- (XI): 2-(6-fluoro-1H-indol-3-yl)-N-(3-((2,3,3-trifluoroprop-1-en-1-yl)oxy)benzyl)ethan-1-amine Example 1: Synthesis of Compound (V) from Compound (III) and Compound (IV)

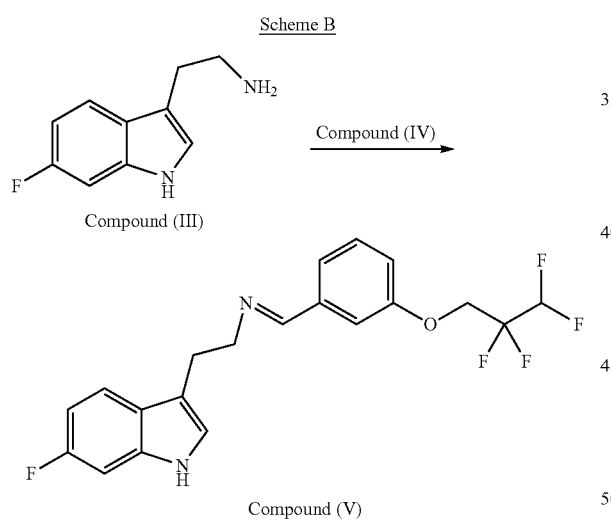

In IPA as Solvent:

A mixture of Compound (III) (78 g, 0.438 mol) and Compound (IV) (114 g, 0.483 mol) in IPA (1480 mL) was heated at 70-75° C. for 3 h with stirring. The reaction mixture was then cooled to 40° C. with stirring, and seeded with Compound (V) and then subsequently allowed to cool slowly to rt over a period of 2 h, and stirred overnight at rt. The resulting suspension was filtered, and the filtercake was washed with IPA (100 mL) and dried in vacuum at 40° C. to yield Compound (V) (142 g, 82%) as a solid, with >99% purity according to $^1$H NMR analysis.

Analytical data for Compound (V): $^1$H NMR (600 MHz, CDCl$_3$) $\delta_H$ 3.14 (t, J=7.0 Hz, 2H), 3.92 (t, J=7.0 Hz, 2H), 4.38 (t, J=12.0 Hz, 2H), 6.07 (tt, J=5.0, 53.0 Hz, 1H), 6.88 (dt, J=2.5, 9.0 Hz, 1H), 6.99 (s, 1H), 7.00 (dd, J=2.5, 8.5 Hz, 1H), 7.02 (dd, J=2.5, 9.5 Hz, 1H), 7.50 (d, J=7.5 Hz, 1H), 7.34 (d, J=8.0 Hz, 1H), 7.35 (m, 1H), 7.54 (dd, J=5.5, 8.5 Hz, 1H), 8.00 (bs, 1H), 8.12 (s, 1H); $^{13}$C NMR (150 MHz, DMSO-d$_6$) $\delta_C$ 26.9, 62.1, 65.4 (t, J=30.0 Hz), 97.5 (d, J=26.0 Hz), 108.1 (d, J=24.5 Hz), 109.1 (tt, J=34.0, 248.5 Hz), 112.0, 114.3, 114.6 (tt, J=27.0, 248.5 Hz), 117.9, 119.8 (d, J=10.5 Hz), 122.4 (d, J=3.0 Hz), 123.3, 124.3, 130.1, 136.2 (d, J=12.5 Hz), 138.1, 157.7, 160.1 (d, J=236.0 Hz), 160.8.

In Toluene as Solvent:

A mixture of Compound (III) (4.50 g, 25.3 mmol) and Compound (IV) (5.96 g, 25.3 mmol) in toluene (45 mL) was heated at reflux for 2 h and water was removed by azeotropical distillation with Dean-Stark water apparatus (volume ~10 mL) attached. The mixture was cooled slowly to rt with stirring, and the formed suspension was filtered. The filtercake was washed with toluene (10 mL), and dried in vacuum at 40° C. to yield Compound (V) (7.68 g, 70%) as a solid.

Example 2: Synthesis of Compound (V) from Crude Compound (II)

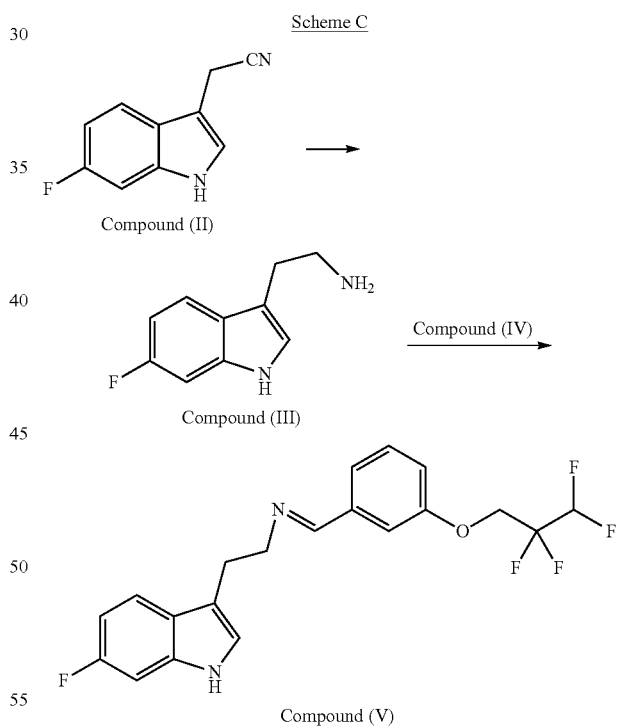

To a solution of crude Compound (II) (10.0 g, 57.4 mmol, 96% UV purity in LC-MS) in aq. ammonia (65 mL, 24% w/w) and IPA (35 mL) was added nickel catalyst (PRICAT type 55/5P from Johnson Matthey Ltd., 2.99 g, 30% w/w) at rt. The mixture was hydrogenated at 4 bar for 20 h at 50° C. The mixture was cooled and filtered through Arbocell BC 200™. The mixture was evaporated to dryness, and more IPA (100 mL) was added. The mixture was again evaporated to dryness to yield crude Compound (III). The crude Com pound (III) (92% UV purity in LC-MS) was dissolved together with Compound (IV) (13.6 g, 57.4 mmol) in IPA (75 mL), and the mixture was heated at 75° C. for 1.5 h. The mixture was cooled with stirring to 45° C. and seeded with Compound (V), and further cooled slowly with stirring to rt, and stirred overnight. The mixture was then cooled at 0° C. for 1 h with stirring, and filtered cold. The filtercake was washed with IPA (10 mL) and dried in vacuum at 40° C. to yield Compound (V) (17.8 g, 78%) as a solid, with >99% purity according to $^1$H NMR analysis.

Example 3: Screening of Catalysts in the Hydrogenation of Compound (V)

General Procedure (for Details, See Table 1-3):

To a solution of Compound (V) in solvent (2 mL) was added catalyst and any additive and the mixture was hydrogenated in an Endeavor hydrogenation apparatus (from Biotage AB) for 24 h. The reaction mixture was subsequently analysed by LC-MS.

TABLE 1

Screening of iridium, rhodium, platinum and ruthenium catalysts

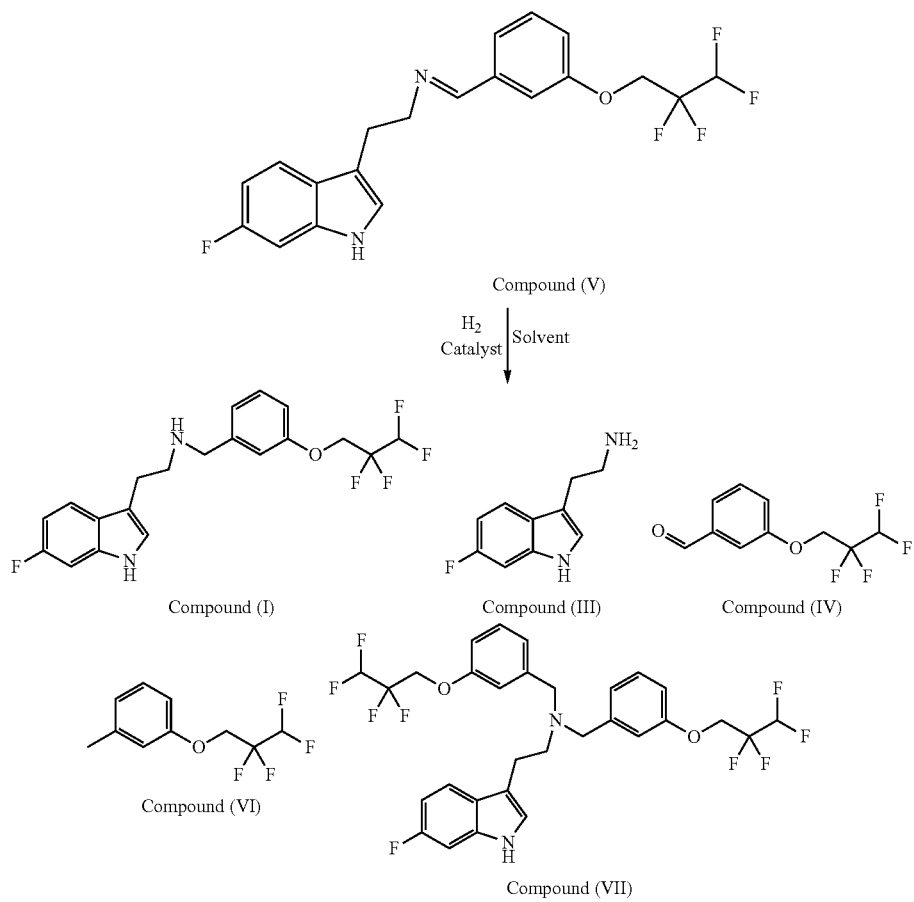

| Entry | Catalyst | Loading[1] | Solvent | Pressure[2] | Temperature[3] | (III)[4] | (IV)[4] | (VI)[4] | (VII)[4] | (I)[4] |
|---|---|---|---|---|---|---|---|---|---|---|
| 1 | Ir/CaCO$_3$[5] | 0.5 | EtOAc | 4 | 60 | <1 | <1 | ND | ND | 98 |
| 2 | Ir/CaCO$_3$[5] | 0.5 | IPA | 4 | 60 | <1 | <1 | ND | ND | 98 |
| 3 | Ir/CaCO$_3$[5] | 0.5 | Toluene | 4 | 60 | <0.5 | <0.5 | ND | ND | 99 |
| 4 | Ir/CaCO$_3$[5] | 0.5 | IPA-toluene[7] | 4 | 60 | <0.5 | <0.5 | ND | ND | 99 |
| 5 | 5% Rh/Al[6] | 2 | THF | 1 | 25 | 16 | 67 | ND | ND | 16 |
| 6 | 5% Rh/Al[6] | 2 | EtOAc | 1 | 25 | 16 | 65 | ND | ND | 19 |
| 7 | 5% Rh/Al[6] | 2 | IPA | 1 | 25 | 15 | 63 | ND | ND | 22 |
| 8 | 5% Rh/Al[6] | 2 | Toluene | 1 | 25 | 18 | 77 | ND | ND | 5 |
| 9 | 5% Rh/Al[6] | 2 | IPA-toluene[7] | 1 | 25 | 12 | 47 | ND | ND | 41 |
| 10 | Pt/C[8] | 0.1 | THF | 4 | 25 | ND | ND | ND | ND | >99 |
| 11 | Pt/C[8] | 0.1 | EtOAc | 4 | 25 | 1 | 3 | ND | ND | 94 |
| 12 | Pt/C[8] | 0.1 | IPA | 4 | 25 | ND | ND | ND | ND | >99 |
| 13 | Pt/C[8] | 0.1 | Toluene | 4 | 25 | ND | ND | ND | ND | >99 |
| 14 | Pt/C[8] | 0.1 | IPA-toluene[7] | 4 | 25 | ND | ND | ND | ND | >99 |
| 15 | Ru/C[9] | 0.5 | Toluene | 4 | 90 | 18 | 74 | ND | 1 | 7 |
| 16 | Ru/C[9] | 0.5 | Toluene | 4 | 100 | 18 | 74 | ND | 1 | 7 |
| 17 | Ru/C[9] | 0.5 | Toluene | 4 | 110 | 17 | 60 | ND | 3 | 20 |

TABLE 1-continued

| 18 | Ru/C[9] | 1.0 | Toluene | 4 | 110 | 12 | 40 | ND | 6 | 42 |
| 19 | Ru/C[9] | 2.0 | Toluene | 4 | 110 | 5 | 5 | ND | 8 | 82 |

[1]In mol %;
[2]In bar;
[3]In ° C.;
[4]Yields (in %) from LC-MS analysis at 254 nm (UV);
[5]Type 30 from Johnson Matthey Ltd.;
[6]Type 524 from Johnson Matthey Ltd.;
[7]1:1 v/v mixture;
[8]Type 128M from Johnson Matthey Ltd.;
[9]Type 600 from Johnson Matthey Ltd.

TABLE 2

Screening of copper catalysts[1]

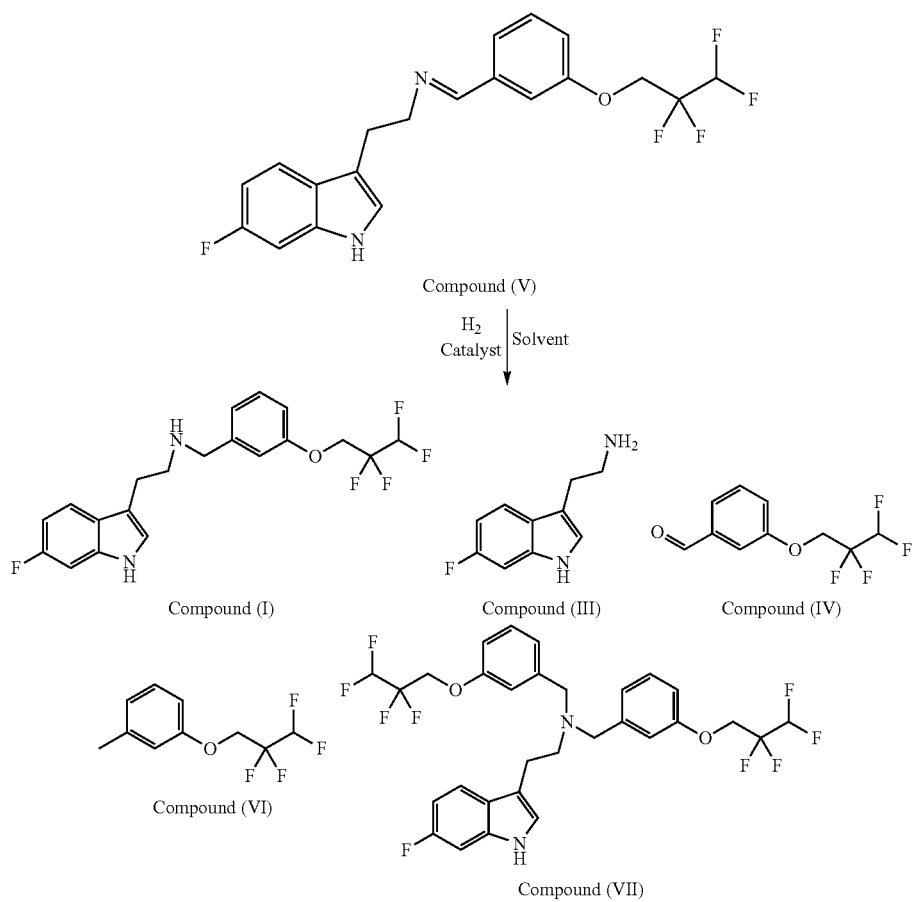

| Entry | Catalyst | Loading[2] | Solvent | (III)[3] | (IV)[3] | (VI)[3] | (VII)[3] | (I)[3] |
|---|---|---|---|---|---|---|---|---|
| 1 | PRICAT CU 50/8 | 15 | THF | 18 | 76 | ND | 5 | 1 |
| 2 | PRICAT CU 50/8 | 15 | EtOAc | 10 | 47 | ND | 3 | 40 |
| 3 | PRICAT CU 50/8 | 15 | IPA | 3 | 0 | ND | 12 | 78 |
| 4 | PRICAT CU 50/8 | 15 | Toluene | 18 | 77 | ND | ND | 5 |
| 5 | PRICAT CU 50/8 | 15 | IPA-Toluene[4] | 19 | 78 | ND | ND | 3 |
| 6 | PRICAT CU 60/8 | 15 | THF | 17 | 73 | ND | ~1 | 9 |
| 7 | PRICAT CU 60/8 | 15 | EtOAc | 15 | 63 | ND | ND | 22 |
| 8 | PRICAT CU 60/8 | 15 | IPA | 17 | 66 | ND | ND | 16 |
| 9 | PRICAT CU 60/8 | 15 | Toluene | 16 | 75 | ND | ~1 | 6 |
| 10 | PRICAT CU 60/8 | 15 | IPA-Toluene[4] | 19 | 80 | ND | <1 | <1 |
| 11 | Cu/C[5] | 100 | Toluene | 4 | 38 | 2 | ND | 54 |
| 12 | Cu/C[5] | 100 | EtOH | 6 | 40 | 2 | 3 | 50 |

TABLE 2-continued

| | | | | | | | | |
|---|---|---|---|---|---|---|---|---|
| 13 | Cu/C[5] | 100 | EtOAc | 6 | 34 | 2 | 2 | 57 |
| 14 | Copper powder[6] | 100 | THF | 19 | 80 | ND | ND | ~1 |
| 15 | Copper powder[6] | 100 | EtOAc | 4 | 21 | ND | ND | 74 |
| 16 | Copper powder[6] | 100 | IPA | ND | ND | ND | Trace | 95 |
| 17 | Copper powder[6] | 100 | Toluene | 18 | 79 | ND | ND | ~2 |
| 18 | Copper powder[6] | 100 | IPA-Toluene[4] | 12 | 48 | ND | 3 | 37 |
| 19 | Copper nanopowder[7] | 100 | THF | ND | ND | ND | ND | 94 |
| 20 | Copper nanopowder[7] | 100 | EtOAc | 17 | 60 | 0 | 3 | 20 |
| 21 | Copper nanopowder[7] | 100 | IPA | ND | ND | ND | ND | 75 |
| 22 | Copper nanopowder[7] | 100 | Toluene | ND | ND | ND | ND | >97% |
| 23 | Copper nanopowder[7] | 100 | IPA-Toluene[4] | ND | ND | ND | ND | 86 |

[1]All reactions performed at 4 bar pressure and 100° C.;
[2]In % w/w relative to Compound (V);
[3]Yields (in %) from LC-MS analysis at 254 nm (UV);
[4]1:1 v/v mixture;
[5]3% w/w copper nanoparticles in carbon, from Sigma-Aldrich Inc., item #709107;
[6]From Sigma-Aldrich Inc., item #292583, +45 µM;
[7]Type Cu N100 from Tekmat Inc.

TABLE 3

Screening of palladium catalysts[1]

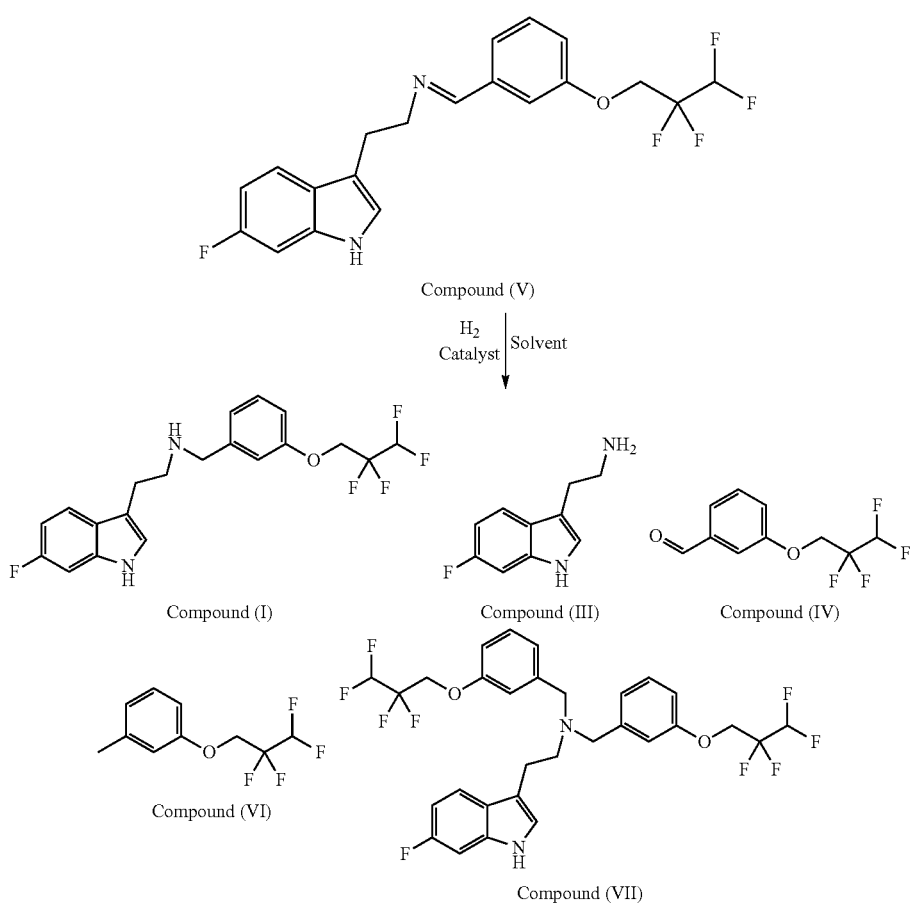

| Entry | Catalyst | Loading[2] | Additive | Solvent | Temperature[3] | (III)[4] | (IV)[4] | (VI)[4] | (VII)[4] | (I)[4] |
|---|---|---|---|---|---|---|---|---|---|---|
| 1 | 5% Pd/C[5] | 0.5 | None | IPA-Toluene[6] | 25 | 2 | ND | ~1 | ND | 95 |
| 2 | 5% Pd/C[5] | 0.1 | None | THF | 25 | ND | ND | ND | ND | 99 |

TABLE 3-continued

| | | | | | | | | | | |
|---|---|---|---|---|---|---|---|---|---|---|
| 3 | 5% Pd/C[5] | 0.1 | None | EtOAc | 25 | <1 | 1 | ND | ND | 98 |
| 4 | 5% Pd/C[5] | 0.1 | None | IPA | 25 | 3 | 13 | ND | ND | 84 |
| 5 | 5% Pd/C[5] | 0.1 | None | Toluene | 25 | 11 | 51 | ND | ND | 37 |
| 6 | 5% Pd/C[5] | 0.1 | None | IPA-Toluene[6] | 25 | ND | ND | ND | ND | >99 |
| 7 | 5% Pd/C[5] | 0.05 | None | IPA-Toluene[6] | 25 | 14 | 40 | ND | ND | 46 |
| 8 | 5% Pd/C[5] | 0.05 | None | IPA-Toluene[6] | 50 | Trace | 3 | ND | ND | 97 |
| 9 | 5% Pd/C[5] | 0.05 | None | IPA-Toluene[6] | 80 | ND | ND | ND | ND | >99 |
| 10 | 5% Pd/C[5] | 0.1 | AcOH (2 eq) | IPA-Toluene[6] | 25 | 2 | 3 | ND | ND | 94 |
| 11 | 5% Pd/C[5] | 0.05 | AcOH (2 eq) | IPA-Toluene[6] | 25 | 2 | 3 | ND | ND | 95 |
| 12 | 5% Pd/C[5] | 0.05 | MsOH (2 eq) | IPA-Toluene[6] | 25 | ~0.5 | ND | ND | ND | 98 |
| 13 | Pd-Cu/C[7] | 1 | None | IPA-Toluene[6] | 25 | ~1 | 4 | ND | ND | 96 |

[1]All reactions were performed at 1 bar pressure;
[2]In mol %;
[3]In ° C.;
[4]Yields (in %) from LC-MS analysis at 254 nm (UV);
[5]Type 338 from Johnson Matthey Ltd.;
[6]1:1 v/v mixture;
[7]Type A701023-4 from Johnson Matthey Ltd.

Example 4: Synthesis of Compound (I) as HCl-Salt from Compound (V)

A mixture of Compound (V) (10.0 g, 25.2 mmol) and 5% Pd/C catalyst (type 5R338 from Johnson Matthey Ltd., 59.4% w/w water, 0.265 g, 0.050 mmol) in toluene (50 mL) and IPA (50 mL) was hydrogenated at rt and 1 bar for 3 h. The reaction mixture was filtered through Arbocell BC 200™, and the filtrate was evaporated to dryness to yield Compound (I). Compound (I) was dissolved in IPA (30 mL) and toluene (70 mL), and aq. HCl (2.7 mL, 32.8 mmol, 37% w/w) was added dropwise at rt with vigorous stirring. Then more toluene (100 mL) was added and the mixture was concentrated to approx. 50% of the original volume. The formed suspension was filtered, and the precipitate was washed with toluene, and dried in vacuum at 40° C. to yield Compound (I) as HCl-salt (1:1) (10.3 g, 94%) as a solid, with 99% UV purity in LC-MS analysis.

Example 5: Synthesis of Compound (I) as HCl-Salt from Compound (III) and (IV)

To a mixture of Compound (III) (4.50 g, 25.3 mmol) and Compound (IV) (5.96 g, 25.3 mmol in toluene (50 mL) and IPA (50 mL) was added 5% Pd/C catalyst (type 5R338 from Johnson Matthey Ltd., 59.4% w/w water, 0.265 g, 0.050 mmol), and the mixture thereafter hydrogenated at rt and 1 bar hydrogen for 23 h. The reaction mixture was filtered through Arbocell BC 200™, and the filtrate was evaporated to dryness to yield Compound (I). Compound (I) was dissolved in IPA (30 mL) and toluene (70 mL), and aq. HCl (2.7 mL, 32.8 mmol, 37% w/w) was added dropwise at rt with vigorous stirring. Then more toluene (100 mL) was added and the mixture was concentrated to approx. 50% of the original volume. The formed suspension was filtered, and the precipitate was washed with toluene, and dried in vacuum at 40° C. to yield Compound (I) as HCl-salt (1:1) (9.59 g, 87%) as a solid, with 94% UV purity in LC-MS analysis.

Example 6: Synthesis of Compound (I) as HCl-Salt from Compound (III) and (IV)

A mixture of Compound (III) (11.0 g, 62 mmol) and Compound (IV) (14.4 g, 59 mmol) was heated in toluene (120 mL) and isopropanol (96 mL) at 75° C. for 3 h. The mixture was allowed to cool to room temperature, and 3% Pt/C (type Noblyst P8080 from Evonik, 61.2% w/w water, 3.06 g, 0.183 mmol) was added. The mixture was hydrogenated at 70-75° C. and 5 bar for 6 h. The reaction mixture was cooled, filtered and the filtrate was evaporated to dryness to yield crude Compound (I) (25.7 g). The crude Compound (I) (24.7 g used, 1 g kept for analysis) was dissolved in toluene (205 mL) at rt and the organic layer was washed twice with a 2% sodium hydroxide solution (79 mL), followed by washing with a mixture of 3% solution of ammonium chloride (74 mL) and water (74 mL). A solution of diluted hydrochloric acid (prepared from 6.4 mL 37% w/w aq. HCl and 21.3 mL water) was added over a period of 10 min. Acetonitrile (20 mL) was added and the mixture was heated to 50° C. Upon cooling to 30° C. Compound (I) as HCl-salt (1:1) precipitated, and it was isolated by filtration at rt, and washed with a mixture of toluene/acetonitrile, dilute HCl and water. The wet product was dried at 65° C. under vacuum overnight providing dry Compound (I) as HCl salt (1:1) (20.4 g, 47 mmol, 83% yield corrected for 1 g sample taken), with 99.1% UV purity in HPLC analysis.

Example 7: Reprecipitation of Compound (I) as HCl-Salt (1:1)

A suspension of Compound (I) as HCl salt (1:1) (20.0 g, 99.1% UV purity in HPLC analysis) in toluene (160 mL) and acetonitrile (60 mL) was heated to 73° C. to obtain dissolution and then cooled to 51° C., seeded with Compound(I) as HCl salt (1:1) (100 mg), and further cooled to 20° C. The formed suspension was filtered, and the filter cake was washed with a mixture of toluene/acetonitrile. The wet product was dried at 65° C. under vacuum providing dry Compound (I) as HCl-salt (1:1) (17.5 g, 88%), with 99.7% UV purity in HPLC analysis.

The invention claimed is:
1. A process for the preparation of N-(2-(6-fluoro-1H-indol-3-yl)-ethyl)-3-(2,2,3,3 tetrafluoropropoxy)-benzylamine (Compound (I)), and pharmaceutically acceptable salts thereof, comprising the steps of:

(1) reacting Compound (III) and Compound (IV) in a solvent or solvent mixture, with or without removal of water, to thereby form a reaction mixture that comprises Compound (V), and (2) reacting the Compound (V) of the reaction mixture formed in step (1) with hydrogen in the presence of a transition metal catalyst in a solvent or a solvent mixture with or without the presence of a first acid to form said Compound (I), and (3) optionally adding a second acid to precipitate said formed Compound (I) as a salt, wherein said Compound (I), Compound (III), Compound (IV) and Compound (V) are:

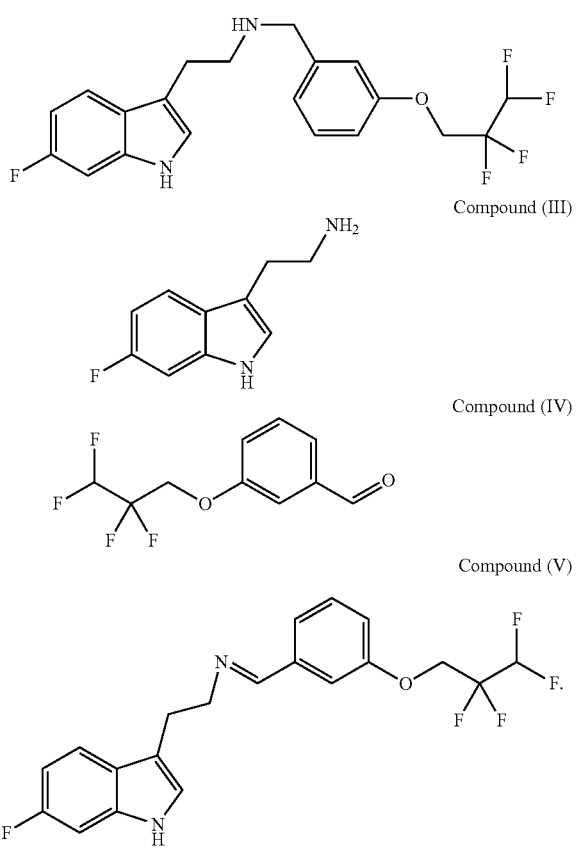

2. A process according to claim 1 wherein said step (1) further comprises cooling the reaction mixture to precipitate Compound (V) as a solid and Compound (V) is isolated.

3. The process according to claim 1, wherein Compound (V) is formed in an alcoholic solvent.

4. The process according to claim 3, wherein said alcoholic solvent is 2-propanol.

5. The process according to claim 1, wherein Compound (V) is formed in a hydrocarbon solvent.

6. The process according to claim 5, wherein said hydrocarbon solvent is toluene or heptane or a mixture of toluene and heptane.

7. The process according to claim 1, wherein water is removed by azeotropical separation in step (1).

8. The process according to claim 1, wherein the temperature in which Compound (V) is formed is between 0° C. and 100° C.

9. The process according to claim 2, wherein precipitation of Compound (V) is done by cooling the mixture to between −10° C. and 30° C.

10. The process according to claim 1, wherein the purity of Compound (III) and Compound (IV) is in the range of 90%-99%.

11. The process according to claim 2, wherein the hydrogenation is carried out in a solvent comprising an ether, ester, alcohol, hydrocarbon or a solvent mixture consisting of at least two solvents independently selected from an ether, ester, alcohol, or hydrocarbon.

12. The process according to claim 1, wherein the hydrogenation of Compound (V) is carried out at a hydrogen pressure of 1 bar to 10 bar.

13. The process according to claim 1, wherein the transition metal catalyst comprises iridium, rhodium, platinum, ruthenium, copper or palladium.

14. The process according to claim 13, wherein the transition metal catalyst is supported on silicium oxide, alumina, carbon or mixtures thereof.

15. The process according to claim 1, wherein the hydrogenation is carried out in the presence of the first acid, wherein the first acid is one or more acids selected from the group consisting of acetic acid, methane sulfonic acid, trifluoracetic acid, hydrochloric acid, and sulfuric acid.

16. The process according to claim 1, wherein Compound (I) is precipitated as a salt by addition of the second acid to obtain the corresponding acid addition salt.

17. The process according to claim 1, wherein Compound (I) is precipitated as a 1:1 HCl salt.

18. A process for the preparation of Compound (V)

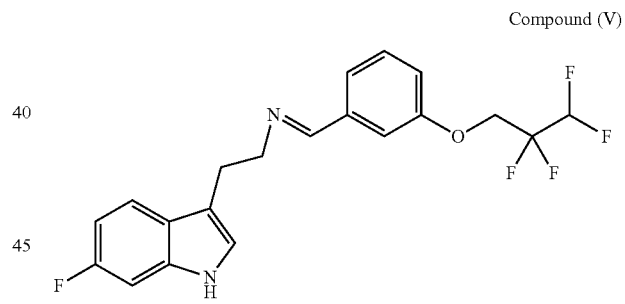

comprising the steps of:
(a) Mixing Compound (III) and Compound (IV) in a solvent or solvent mixture, with or without azeotropical separation of water to thereby form Compound (V);
(b) Precipitating said formed Compound (V); and
(c) Isolating the precipitated Compound (V);
wherein said Compound (III) and Compound (IV) are:

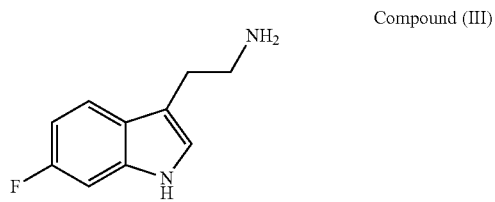

-continued
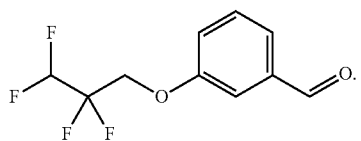
Compound (IV)
* * * * *

UNITED STATES PATENT AND TRADEMARK OFFICE
CERTIFICATE OF CORRECTION

PATENT NO. : 9,975,850 B2
APPLICATION NO. : 15/480647
DATED : May 22, 2018
INVENTOR(S) : Mikkel Fog Jacobsen et al.

Page 1 of 1

It is certified that error appears in the above-identified patent and that said Letters Patent is hereby corrected as shown below:

In the Claims

At Column 18, Claim number 1, Line number 65 should read:
A process for the preparation of N-(2-(6-fluoro-1H-indol-3-yl)-ethyl)-3-(2,2,3,3-tetrafluoropropoxy)-benzylamine (Compound (I)), and pharmaceutically acceptable salts thereof, comprising the steps of:
(1) reacting Compound (III) and Compound (IV) in a solvent or solvent mixture, with or without removal of water, to thereby form a reaction mixture that comprises Compound (V), and
(2) reacting the Compound (V) of the reaction mixture formed in step (1) with hydrogen in the presence of a transition metal catalyst in a solvent or a solvent mixture with or without the presence of a first acid to form said Compound (I), and
(3) optionally adding a second acid to precipitate said formed Compound (I) as a salt, wherein said Compound (I), Compound (III), Compound (IV) and Compound (V) are:

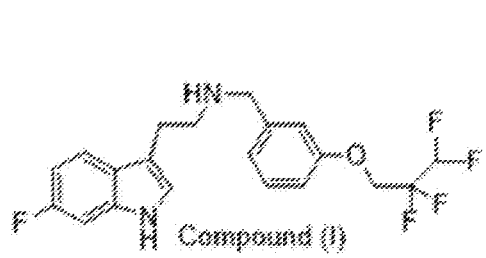
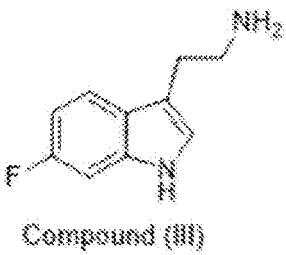
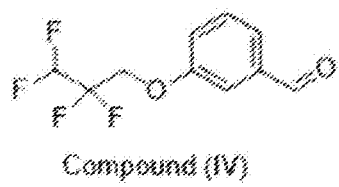
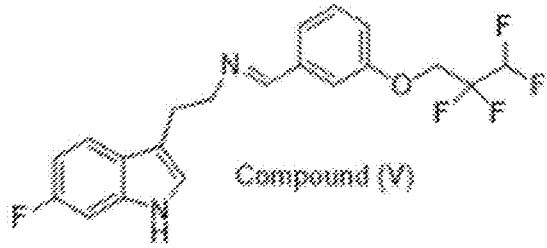

Signed and Sealed this
Third Day of July, 2018

Andrei Iancu
*Director of the United States Patent and Trademark Office*